US007235247B2

(12) United States Patent
Nishibe et al.

(10) Patent No.: US 7,235,247 B2
(45) Date of Patent: Jun. 26, 2007

(54) PHARMACEUTICAL COMPOSITION FOR APPLICATION TO MUCOSA

(75) Inventors: Yoshihisa Nishibe, Hino (JP); Wataru Kinoshita, Hino (JP); Hiroyuki Kawabe, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 0 days.

(21) Appl. No.: 10/201,303

(22) Filed: Jul. 24, 2002

(65) Prior Publication Data
US 2003/0008019 A1    Jan. 9, 2003

Related U.S. Application Data

(63) Continuation of application No. 09/446,276, filed as application No. PCT/JP99/02126 on Apr. 21, 1999, now Pat. No. 6,939,559.

(30) Foreign Application Priority Data
Apr. 21, 1998  (JP)  ................... 10-110887
Apr. 21, 1998  (JP)  ................... 10-110888

(51) Int. Cl.
A61K 9/10    (2006.01)
A61F 2/02    (2006.01)
A61F 2/14    (2006.01)
A61F 6/06    (2006.01)
A61F 13/02   (2006.01)

(52) U.S. Cl. ............ 424/400; 423/400; 423/423; 423/427; 423/430; 423/434; 423/435

(58) Field of Classification Search ............ 424/434, 424/424, 400, 435, 430, 427, 423
See application file for complete search history.

(56) References Cited

U.S. PATENT DOCUMENTS

| 4,271,143 A | 6/1981 | Schoenwald et al. |
| 4,613,500 A | 9/1986 | Suzuki et al. |
| 4,615,697 A | 10/1986 | Robinson |
| 4,988,512 A | 1/1991 | Azria |
| 5,147,654 A | 9/1992 | Place et al. |
| 5,179,079 A | 1/1993 | Hansen et al. |
| 5,188,826 A | 2/1993 | Chandrasekaran et al. |
| 5,192,535 A | 3/1993 | Davis et al. |
| 5,200,195 A | 4/1993 | Dong et al. |
| 5,281,580 A * | 1/1994 | Yamamoto et al. ........... 514/12 |

(Continued)

FOREIGN PATENT DOCUMENTS

CA    2107587 A1    10/1992

(Continued)

OTHER PUBLICATIONS

Sax's Dangerous Properties of Industiral Materials (10th Edition) vols. 1-3, Lew, Richard J., Sr, John Wiley & Sons, 2000.*

(Continued)

Primary Examiner—Carlos A. Azpuru
(74) Attorney, Agent, or Firm—Sughrue Mion, PLLC

(57) ABSTRACT

The present invention provides a pharmaceutical composition for application to the mucosa to be used in drug therapy comprising a water-insoluble and/or water-low soluble substance, a medicament, and an aqueous medium, and having an osmotic pressure of less than 290 mOsm. This composition is superior over conventional pharmaceutical compositions for application to the mucosa, due to efficient and high permeability to the blood at the mucosa. The present invention further provides a pharmaceutical composition for application to the mucosa comprising a hemostatic agent and a medicament. This composition is superior over conventional pharmaceutical compositions for application to the mucosa, due to permeability and retentivity at the mucosa.

29 Claims, 4 Drawing Sheets

U.S. PATENT DOCUMENTS

| | | | |
|---|---|---|---|
| 5,340,572 | A | 8/1994 | Patel et al. |
| 5,393,773 | A | 2/1995 | Craig et al. |
| 5,474,764 | A | 12/1995 | Patel et al. |
| 5,474,768 | A | 12/1995 | Robinson |
| 5,733,569 | A | 3/1998 | Azia et al. |
| 5,869,096 | A | 2/1999 | Barclay et al. |
| 5,942,242 | A | 8/1999 | Mizushima et al. |
| 5,976,573 | A * | 11/1999 | Kim .......................... 424/400 |

FOREIGN PATENT DOCUMENTS

| | | |
|---|---|---|
| CA | 1327314 A1 | 3/1994 |
| CA | 2164624 A1 | 1/1995 |
| CA | 2268140 A1 | 4/1998 |
| CA | 2278025 A1 | 7/1998 |
| EP | 0 496 308 A1 | 7/1992 |
| EP | 496 308 A1 * | 7/1992 |
| EP | 0781546 A1 | 12/1996 |
| HU | 209 247 B | 4/1994 |
| JP | 59-130820 A | 7/1984 |
| JP | 60-224616 A | 9/1985 |
| JP | 63-303031 | 12/1988 |
| JP | 63-303931 * | 12/1988 |
| JP | 2-262526 | 10/1990 |
| JP | 6-172199 A | 6/1994 |
| JP | 7-188059 | 7/1995 |
| JP | 8-217678 A | 8/1996 |
| JP | 9-25238 | 1/1997 |
| JP | 9-235220 | 9/1997 |
| JP | 63-166832 A | 7/1998 |
| JP | 88106305 | 4/1999 |
| RU | 112102979 | 11/1998 |
| RU | 11829 | 12/2000 |
| WO | WO 92/14473 | 9/1992 |
| WO | WO 97/01337 | 1/1997 |
| WO | WO 97/31626 A1 | 9/1997 |
| WO | WO 98/00178 A1 | 1/1998 |

OTHER PUBLICATIONS

Merck Index, "polysorbate 80", 1989.*
Abstract—"Nasal absorption of propranolol from different dosage forms by rats and dogs" J Pharm Sci Dec. 1980; 69;(12): 1411-3.
Abstract—"Nasal absorption of testosterone in rats" J Pharm Sci Sep. 1984; 73(9): 1300-1.
Abstract—"The time of onset of action of sublingual nitroglycerin in exercise-induced angina pectoris. A methodological study" Eur Hear J Jul. 1985; 6(7): 625-30.
Abstract—"Intranasal delivery of nicardipine in the rat" J Pharm Sci Jan. 1986; 75(1):44-6.
Abstract—"Comparison of the metabolism of diltiazem following percutaneous, subcutaneous, oral and intravenous administration." Drug Des Deliv Nov. 1986; 1(2):151-6.
Abstract—"Comparison of bioavailability in man of tamoxifen after oral and rectal administration" J Pharm Pharmacol Dec. 1986; 38(12): 888-92.
Abstract—"Absolute bioavailability of hydromorphone after peroral and rectal administration in humans: saliva/plasma ratio and clinical effects" J Clin Pharmacol Sep. 1987; 27(9): 647-53.
Abstract—"Pharmacodynamics of acute intranasal administration of verapamil: comparison with i.v. and oral administration." Biopharm Drug Dispos Oct.-Dec. 1985; 6(4): 447-54.
Abstract—"Absolute bioavailability of hydromorphone after peroral and rectal administration in humans: saliva/plsma ration and clinical effects." J Clin Pharmacol Sep. 1987; 27(9): 647-53.
Abstract—"Pharmacokinetics of hydromorphone after intravenous, peroral and rectal administration to human subjects." Biopharm Drug Dispos Mar.-Apr. 1988; 9(2): 187-99.
Abstract—"Pharmacokinetics of bioavailability of hydromorphone: effectof various routes of administration." Pharm Res Nov. 1988; 5(11): 718-21.
Abstract—"Nasal absorption of 17-alpha-ethinyloestradiol in the rat." J Pharm Pharmacol Mar. 1989; 41(3): 214-5.
Abstract—"Nasal absorption of tetraethylammonium in rats." Arch Int Pharmacodyn Ther Nov.-Dec. 1989; 302:7-17.
Abstract—"Pharmacokinetic study of neostigmine after intranasal and intravenous administration in the guinea pig." Drugs Exp Clin Res 1990; 16(11):575-9.
Abstract—"Asthma therapy: present trends and future prospects." Compr Ther Mar. 1990; 16(3):12-6.
Abstract—"Transdermal nitroglycerin systems: methods for comparison." Clin Ther May-Jun. 1991; 13(3): 361-7.
Abstract—"Intranasal absorption of physostigmine and arecoline." J Pharm Sci Aug. 1991; 890(8):750-1.
Abstract—"A ocmparative evaluation of two transdermal nitroglycerin delivery systems: Nitro-Dur versus Transderm-Nitro. The collaborative Investigation Group." Clin Ther Sep.-Oct. 1991; 13(5): 545-9.
Abstract—"Pharmacokinetics and bioavailability of papaverine HCI following intravenous, peroral, rectal, vaginal, topical and buccal administration in beagle dogs." Biopharm Drug Dispos Oct. 1991; 12(7): 537-46
Abstract—"Pharmacokinetics and bioavalability of papaverine HCI after intravenous, intracorporeal and penis topical administration in beagle dogs." Method Find Exp Clin Pharmacol Jun. 1992; 14(5): 373-8.
Abstract—"Enhanced absorption of bumetanide from suppositories containing weak acids in rabbits." Biol Pharm Bull Mar. 1993; 16(3): 263-7.
Abstract—"Studies on the nasal absorption of gentamycin." Chung Hua Erh Pi Yen Hou Ko Tsa Chih 1994; 29(3): 134-6.
Abstract—"Pharamacokinetics and endometrial effects of vaginal administration of mocronized progesterone in an oil-based solution to postmenopausal women." Fertil Steril Apr. 1996; 65(4): 860-2.
Abstract—"Colonic mucus, smoking and ulcertavie colitis" Ann R. Coll Surg Engl Mar. 1996; 78(2):85-91.
Abstract—"Studies on the response of nitroglycerin oral spray compared with sublingual tablets for angina pectoris patients with dry mouth. A multicenter trial." Arzneimittelforschung Feb. 1997; 47(2); 128-31.
Abstract—"Oral transmucosal fentanyl citrate: randomized, double-blinded, placebo-controlled trial for treatment of breakthrough pain in cancer patients." J Natl Cancer Inst Apr. 15, 1998; 90(8):611-6.
Machida Minoru, et al. "Effects of Surfactants and Protease Inhibitors on Nasal Absorption of Recombinant Human Granulocyte Colony-Stimulating Factor (rhG-CSF) in Rats" Biol. Pharm. Bull 17(10) 1375-1378 1994.
Nomura Hideaki, et al. "Effects of a Dosing Solution on the Nasal Absorptionof Non-glycosylated Recombinant Human Granulocyte Colony-Stimulating Factor in Rats" Biol. Pharm. Bull 19(10) 1490-1493 1996.
European Search Report.
New Zealand Examination Report.
Bauer K.H. et al. Pharmazeutische Technologie, Georg Thieme Verlag, Stuttgart, 3rd ed., p. 239.
Dictionary of Food Additives, 1st edition, p. 49-50 (1994), and partial translation.
Dictionary of Food Additives, 1st Edition, (1994), pp. 36-37.
Communication from Ukraine Patent Office dated Nov. 3, 2005, App. No. 2000010301/861M.
Textbook of Pharmacology, 2nd edition, p. 319-320 (1987), and partial translation.
Japanese Office Action.
European Patent Office—Office Action.
Widdicombe, J.H.; Azizi, F.; Pittet, J.F., Transient permeabilization of airway epithelium by mucosal water,: Journal of Applied Physiology, 1996, pp. 491-499, vol. 1, No. 1, USA.
Pujara, Chetan P.; Shao, Zezhi; Duncan, Michelle R.; Mitra, Ashim K., "Effect of formulation variables on nasal epithelial cell integrity: Biochemical evaluations," International Journal of Phramaceutics, 1995, pp. 197-203, vol. 114, No. 2, USA.
Kopell, William N. and Westhead, Edward W., "Osmotic Pressures of Solutions of ATP and Catecholamins Relating to Storage in Chromaffin Granules," The Journal of Biological Chemistry, May 25, 1982, vol. 257, No. 10, pp. 5707-5710, United States of America.

* cited by examiner

Fig.4
(A)
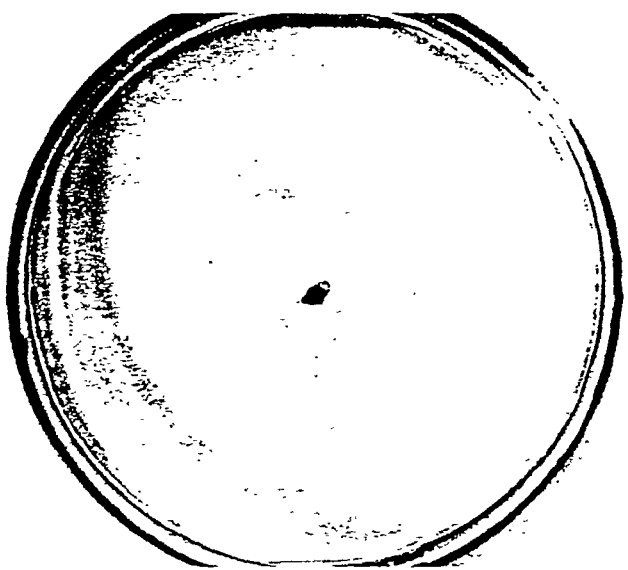
(B)
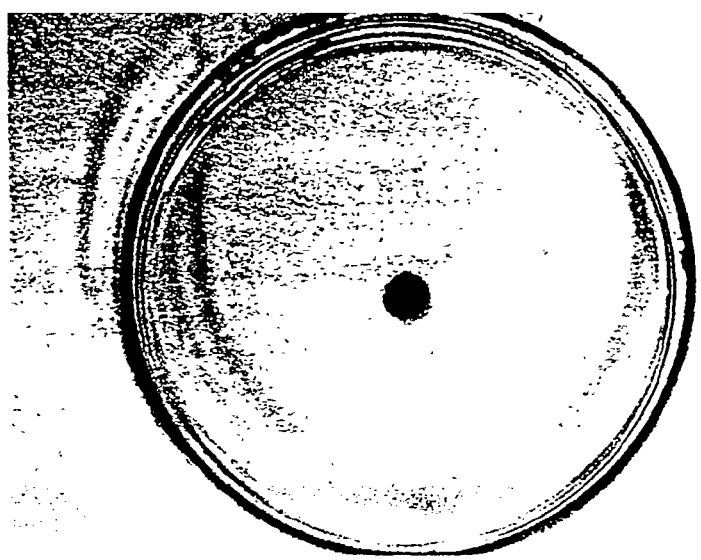

US 7,235,247 B2

PHARMACEUTICAL COMPOSITION FOR APPLICATION TO MUCOSA

This is a Continuation of application Ser. No. 09/446,276, filed Dec. 21, 1999, now U.S. Pat. No. 6,939,559; the disclosure of which is incorporated herein by reference, which is the national Stage of International Application No. PCT/JP99/02126, filed Apr. 21, 1999.

TECHNICAL FIELD

The present invention relates to a pharmaceutical composition for application to the mucosa to be used in drug therapy comprising a water-insoluble and/or low water soluble substance, a medicament, and an aqueous medium, and having an osmotic pressure of less than 290 mOsm. More specifically, the present invention relates to a pharmaceutical composition for application to the mucosa comprising a water-insoluble and/or low water soluble substance, a medicament, and an aqueous medium, and having an osmotic pressure of less than 290 mOsm, that is superior to conventional pharmaceutical compositions for application to the mucosa, due to efficient and high permeability to the blood at the mucosa.

The present invention also relates to a pharmaceutical composition for application to the mucosa comprising a hemostatic agent and a medicament. More specifically, the present invention relates to a pharmaceutical composition for application to the mucosa in which a medicament has been mixed with a hemostatic agent and that is superior over conventional pharmaceutical compositions for application to the mucosa due to high permeability and retention at the mucosa.

BACKGROUND ART

Application to the mucosa as a method of drug therapy has been recognized as a useful means of medication for such reasons as (1) it permits direct application to the affected area for diseases of local areas such as nasal mucosa, oral mucosa, and vaginal mucosa, (2) its immediate effects for systemic diseases can be expected as in the case of a nasal spray to the nasal mucosa and a suppository to the rectal mucosa, and (3) its application is easy compared to injection, as represented by an oral drug targeted at the intestinal mucosa, and the like. For example, pharmaceutical preparations for application to the mucosa have already been commercially available due to reason (1) in the case of nasal sprays for treatment of allergic rhinitis, and due to reason (2) in the case of suppositories to alleviate pain.

As pharmaceutical preparations for local mucus diseases, Saunders et al., (WO 92-14473), for example, provides a suspension preparation containing Tipredane as the main drug as the pharmaceutical preparation for treatment of allergic rhinitis. Also, Helzner (WO 97-01337) provides a pharmaceutical preparation comprising an antihistamic drug, a steroid and water as the pharmaceutical preparation for treatment of allergic rhinitis. As the pharmaceutical preparation for local mucus diseases, furthermore, Kim et al., (WO 98-00178) provides a suspension preparation having a thixotropic property as the pharmaceutical preparation for application to the nasal mucosa. Suzuki et al. (Japanese Examined Patent Publication (Kokoku) No. 60 (1985)-34925) also provides a sustained release pharmaceutical preparation for administration to the nasal cavity that permits the efficient supply of the drug at a concentration sufficient to obtain a therapeutic effect.

As the pharmaceutical preparations for systemic diseases, several methods have been provided that enhance absorption of drugs through the mucosa. Osada et al. (Japanese Unexamined Patent Publication (Kokai) No. 63 (1988)-303931), for example, provides a method of applying to the nasal cavity a growth hormone-releasing factor in liquid form having an osmotic pressure ratio of 1 (an osmotic pressure of 290 mOsm) or lower as a method for enabling quick and efficient absorption of the growth hormone-releasing factor through the nasal mucosa to the blood circulation. Furthermore, Ohwaki et al. (Japanese Unexamined Patent Publication (Kokai) No. 60 (1985)123426) provides a method of applying to the nasal cavity a solution of secretin having an osmotic pressure ratio of 1 to 5 (an osmotic pressure of 290-1450 mOsm) and a pH of 2 to 5 as a method for enabling quick absorption of secretin through the nasal mucosa to blood circulation. Furthermore, Awatsu et al. (Pharm. Res. Vol. 10, No. 9, 1372-1377, 1993) provides a method of applying to the nasal mucosa a pharmaceutical solution to which polyoxyethylene 9-laurylether was added as an absorption enhancer as a method for enabling efficient absorption of a granulocyte colony-stimulating factor through the nasal mucosa to blood circulation.

However, when these pharmaceutical preparations are given to the mucosa, liquid-dripping can occur, or the pharmaceutical preparations are quickly excreted to the outside of the mucus tissue due to a mucociliary clearance function etc. before being adequately transported or permeated to the mucosa tissue. Because of this, the transport of an adequate amount of drug into the blood cannot be effected when systemic administration through transport to the blood circulation is attempted. Furthermore, the method of using an absorption enhancer is yet to be realized because the absorption enhancer has the problem of irritating the nasal mucosa. On the other hand, when local administration is attempted through retention of the drug in the mucosa tissue, an adequate amount of the drug cannot be retained at the tissue. In addition, even if the problem of retentivity has been solved, permeation into the mucosa tissue is not adequate.

Thus, it is strongly desired to develop a pharmaceutical preparation for application to the mucosa, that allows the transport of an adequate amount of the drug through the mucosa to the blood circulation after the application to the mucosa. Alternatively, it is strongly desired to develop a pharmaceutical preparation for application to the mucosa that enables the transport to and retention in the mucosa tissue of an adequate amount of the drug when applied to the mucosa.

DISCLOSURE OF THE INVENTION

Thus, the first object of the present invention is to provide a pharmaceutical composition for application to the mucosa, that has efficient and high permeability through the mucosa to the blood when applied to the mucosa.

The second object of the present invention is to provide a pharmaceutical composition for application to the mucosa, that has efficient and high permeability to the mucosa and retentivity at the mucosa when applied to the mucosa.

After intensive studies to attain the above first object, the present inventors have found that it is possible to provide a pharmaceutical preparation for application to the mucosa that is superior over conventional liquid composition due to efficient and high permeability through the mucosa to the blood, by formulating a drug that contains a water-insoluble and/or low water soluble substance and that has an osmotic pressure of less than 290 mOsm, and thereby have reached the present invention.

An enhanced absorption of a drug through the mucosa by controlling the osmotic pressure of a pharmaceutical preparation is disclosed in a patent to Ohwaki and has been reported in a paper by Awazu et al. (Pharm. Res. Vol. 10, No. 9, 1372-1377, 1993). However, these phenomena are only observed in aqueous solution preparations that do not contain a water-insoluble and/or low water soluble substance, and thereby are essentially different from the pharmaceutical preparation of the present invention in which the inclusion of a water-insoluble and/or low water soluble substance is essential. Furthermore, it has been shown in Osada's patent that absorption through the rat nasal mucosa of growth hormone releasing factor is higher when the preparation has an osmotic pressure ratio of 1 (osmotic pressure of 290 mOsm) or lower, and in Ohwaki's patent it is higher when secretin has an osmotic pressure ratio of 1 (osmotic pressure of 290 mOsm) or greater, and in Awazu's patent the absorption of granulocyte colony-stimulating factor is higher when the preparation has an osmotic pressure of 285 mOsm than 174 mOsm. These observations thereby suggest that it is not easy to think of the present invention that permits enhanced absorption regardless of the type of drug used. In these aqueous solution preparations the degree of enhancement in absorption by controlling osmotic pressure is at most about 3-fold compared to the isotonic pharmaceutical preparations, and therefore the degree of 10 to 20-fold of the present invention is surprising.

The patent application by Saunders (WO 92-14473) and Helzner (WO 97-01337) described above describe pharmaceutical preparations containing a water-insoluble and/or low water soluble substance. However, Saunders' patent application (WO 92-11473) makes no description of osmotic pressure of pharmaceutical preparations in general, in its claim, and merely describes in the specification that isotonicity is preferred, and Helzner's patent application makes no description of osmotic pressure of pharmaceutical preparations in general, and merely describes in the specification that the addition of an isotonic agent is preferred. From these patents, therefore, one cannot expect a drastic enhancement in the absorption at low osmotic pressures.

It is surprising therefore that the effect of enhancing drug absorption through the mucosa is drastic when a water-insoluble or low water soluble substance is coexistent. That is, although there are reports that the effect of low osmotic pressure is observed in some aqueous solution preparations, we have found, surprisingly, that the effect can be observed by adding a water-insoluble or low water soluble substance and the effect does not depend on the type of the drug used.

Thus, in the first aspect, the present invention 5 provides an aqueous pharmaceutical composition for application to the mucosa comprising one or more water-insoluble substance and/or low water soluble substance and one or more medicament, and having an osmotic pressure of less than 290 mOsm. The composition is a pharmaceutical composition for application to the mucosa that is superior over conventional pharmaceutical compositions for application to the mucosa, due to markedly efficient and high permeability to the blood at the mucosa.

After intensive studies to attain the above second object, the present inventors have found that by formulating a pharmaceutical preparation in which a hemostatic agent has been added to a pharmaceutical preparation containing a medicament, a pharmaceutical composition for application to the mucosa having efficient and high permeability to and retentivity at the mucosa can be provided, and thereby have attained the present invention.

Thus, in the second aspect, the present invention 25 provides a pharmaceutical composition for application to the mucosa comprising one or more hemostatic agent and one or more medicament, and more specifically, an aqueous pharmaceutical composition for application to the mucosa comprising one or more hemostatic agent, one or more water-insoluble substance and/or low water soluble substance and one or more medicament, and having an osmotic pressure of less than 290 mOsm. The composition is a pharmaceutical composition for application to the mucosa, that is superior over conventional pharmaceutical compositions for application to the mucosa, due to markedly efficient and high permeability and retentivity at the mucosa.

BRIEF DESCRIPTION OF DRAWINGS

FIG. 4 is a photograph showing the expansion of the composition when the composition of the present invention having an osmotic pressure of 10 mOsm (A) or a composition having an osmotic pressure of 290 mOsm (isotonic pressure) was added to a physiological saline having the same osmotic pressure as the mucus (thereby simulating the mucus) on the mucosa.

EMBODIMENTS FOR CARRYING OUT THE INVENTION

Figure 1:
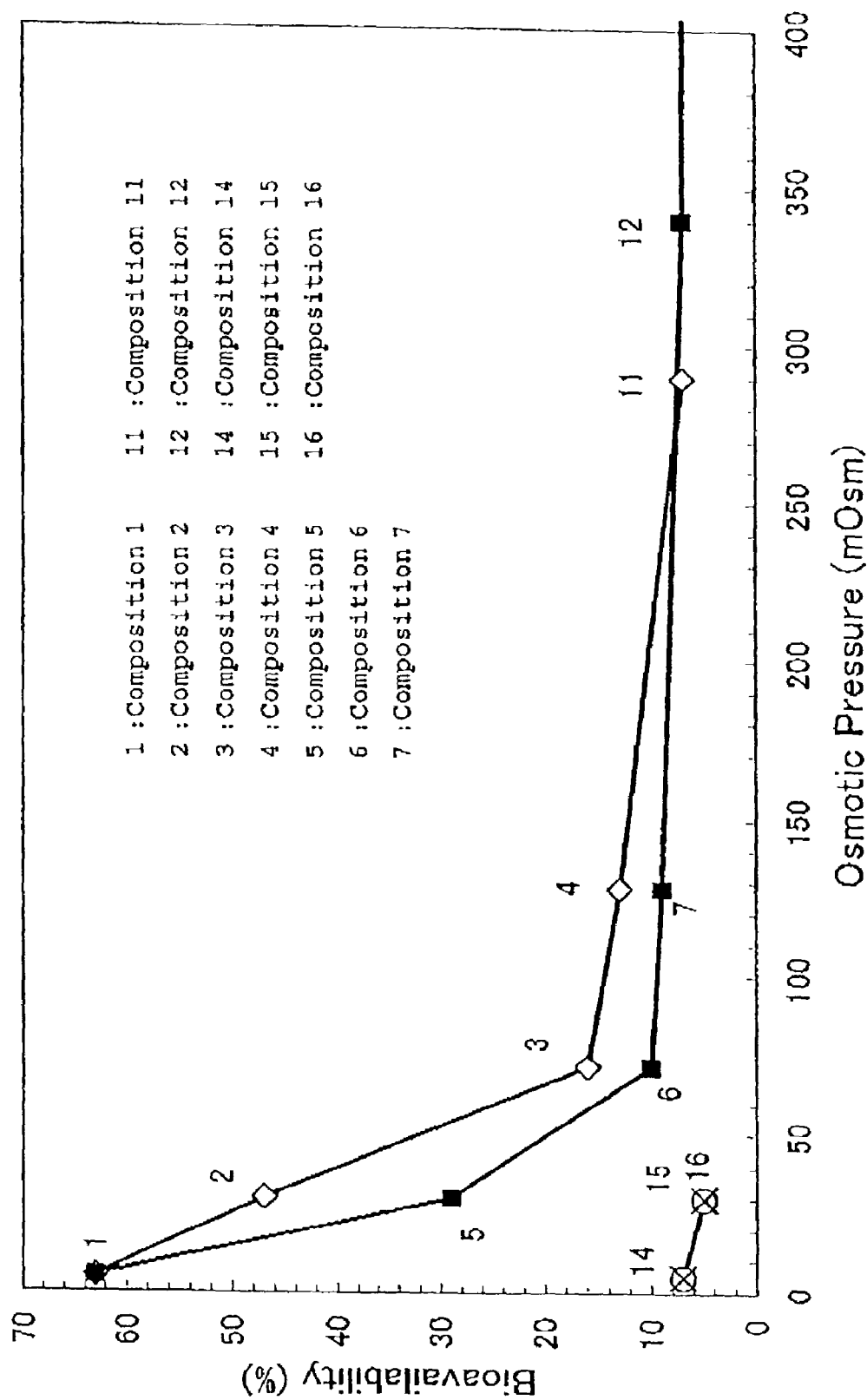
FIG. 1 is a graph showing the relationship between osmotic pressure and bioavailability in the result that compares the absorptivity of fluorescein in Working example 1 and Comparative example 1.

As the medicament of the present invention, any agent can be applied including, for example, one for sedative hypnotics, one for antianxiety drugs, one for anticonvulsants, one for analgesic antipyretics, one for local anesthetics, one for antispasmodics, one for cardiac stimulants, one for diuretics, one for vasoconstrictors, one for vasodilators, one for bronchodilators, one for peptic ulcer drugs, one for analgesics, one for hormone preparations, one for antidotes, one for vaccines, one for antibiotics, one for chemotherapeutics, one for anti-Parkinson drugs, one for psychoneurotics, one for muscle relaxants, one for antiarrhythmic drugs, one for antihypertensive drugs, one for hypolipidemic drugs, one for respiratory stimulants, one for expectorants, one for antiflatuents, one for vitamins, one for antiallergic drugs, and the like. Among them, relatively liposoluble agents are preferred and specific examples include liposoluble vitamins, steroids, and prostaglandins. Among the highly water-soluble agents, those having a high molecular weight are preferred, and specific examples include proteins, and peptides.

Agents that develop beneficial effects when present in the mucosa include, for example, antiallergic drugs such as tranilast, amlexanox, repirinast, ibudilast, tazanolast, pemirolast, oxatomide, azelastine hydrochloride, terfenadine, astemizole, sodium cromoglicate, ketotifen fumarate, emedastine fumarate, epinastine hydrochloride, mequitazine, suplatast tosilate, ozagrel, seratorodast, pranlukast, 5-lipoxygenase inhibitors, and platelet activating antagonists; steroids for rhinitis and asthma such as beclometasone dipropionate, fluticasone propionate, flunisolide, and mometasone; vaccines such as influenza HA vaccine, and; agents for genetic therapy such as antisense, ribozyme, and vectors.

In the first aspect of the present invention, the water-insoluble and/or low water soluble substance is an essential component, and in the second aspect of the present invention, the composition preferably contains a water-insoluble and/or low water soluble substance. Such a water-insoluble or low water soluble substance may be any substance, and preferred examples include celluloses and more preferably crystalline celluloses. The concentration of the water-insoluble and/or low water soluble substance, that is present as solid particles in an aqueous medium in the first aspect of the present invention, is preferably 0.1% w/w or greater relative to the total amount of the preparation, and more preferably 1% to 10% w/w. The concentration of the water-insoluble and/or low water soluble substance that is present as solid particles in an aqueous medium in the second aspect of the present invention is preferably 0.1% w/w or greater relative to the total amount of the preparation, and more preferably 1% to 10% w/w.

In any of the aspects of the present invention, preferably the water-insoluble or low water soluble substance that is present as solid particles in an aqueous medium is homogeneously dispersed in the aqueous medium.

In any of the aspects of the present invention, preferably a water-soluble polymer is further added to the composition. Specifically, alginic acid, propylene glycol, polyethylene glycol, glycerin, polyoxyethylene polyoxypropylene glycol, pectin, low methoxyl pectin, guar gum, gum arabic, carrageenan, methyl cellulose, carboxymethyl cellulose sodium, xanthan gum, hydroxypropyl cellulose, hydroxypropyl methyl cellulose, and the like can be mentioned, and preferably carboxymethyl cellulose sodium, xanthan gum, and hydroxypropyl cellulose can be mentioned. The above polyoxyethylene polyoxypropylene glycol is a series of polymers in which ethylene oxide has been addition-polymerized to a polypropylene glycol obtained by polymerization of propylene oxide, and are classified into several types by the difference in the mean degree of polymerization of propylene oxide and ethylene oxide, with any type being usable in the present invention. In addition, as preferred combinations of a water-soluble polymers and water-insoluble and/or water-low soluble substance, there can be mentioned crystalline cellulose carmellose sodium that is a mixture of carboxymethyl cellulose sodium and crystalline cellulose. Preferably the concentration of these water-soluble polymers, when added, is 1% w/w to 30% w/w relative to the water-insoluble and/or water-low soluble substance.

It is an essential requirement in the first aspect of the present invention that the osmotic pressure of the pharmaceutical preparation is less than 290 mOsm, and preferably it is 150 mOsm or lower, more preferably 60 mOsm or lower, more preferably 30 mOsm or lower, and most preferably 10 mOsm or lower. The control of osmotic pressure is not required in the second aspect of the present invention, but it is preferably lower than the osmotic pressure of the mucus at the mucosa of the targeted administration site, and specifically it is less than 290 mOsm, preferably 150 mOsm or lower, more preferably 60 mOsm or lower, more preferably 30 mOsm or lower, and most preferably 10 mOsm or lower.

In the present invention, the addition of a substance for controlling osmotic pressure (osmotic pressure-controlling agent) is not particularly required, but when it is added any substance can be used. Specific examples include salts such as sodium chloride, and water-soluble sugars such as glucose, and among them salts such as sodium chloride are preferred.

The hemostatic agent for use in the second aspect of the present invention may be any agent, and specific examples include tranexamic acid, epsilon aminocaproic acid, carbazochrome, carbazochrome sulfonate, carbazochrome sodium sulfonate, phytonadione, etamsylate, monoethanol amine oleate, thrombin, hemocoaglase, adrenochrome monoaminoguanidine mesilate, and the like. When the above water-soluble polymer is added, the hemostatic agent or the medicament is preferably highly liposoluble, and specific examples include carbazochrome, carbazochrome sulfonate, and carbazochrome sodium sulfonate as the hemostatic agent, and liposoluble vitamins, steroids, and prostaglandins as the medicament. As the highly water-soluble medicament, a high molecular weight compound is preferred and specific examples include proteins and peptides.

In the present invention, a known surfactant can be added and specific examples include polysorbate 80 (polyoxyethylene (20) sorbitan monooleate), glycerin monostearate, polyoxyl stearate, Lauromacrogol, sorbitan oleate, sucrose fatty acid esters, and the like. Among them, polysorbate 80 is most preferred.

The amount of the medicament for use in the present invention is a therapeutically effective amount and can be determined depending on the type of drug administered, the type and the degree of the disease, the age and the weight of the patient, and the like. It is usually from the same to 20 times as much as the amount of each drug commonly used for injection, more preferably from the same to 10 times as much.

The concentration of the medicament of the present invention is preferably 0.01% w/w to 1% w/w relative to the total amount of the pharmaceutical preparation, and most preferably 0.05% w/w to 0.5% w/w.

In order to improve the physical properties, appearances, or smells of the composition of the present invention, a known antiseptic, a pH controlling agent, a preservative, a buffer, a colorant, a smell corrigent, and the like may be added, as desired. For example, benzalkonium chloride as the antiseptic, hydrochloric acid as the pH controlling agent, ascorbic acid as the preservative, citric acid and salts thereof as the buffer, Red No. 2 as the colorant, menthol as the smell corrigent may be mentioned.

The mucosa to which the present invention is applied may be any mucosa. Specific examples include intestinal mucosa, gastric mucosa, nasal mucosa, tracheal/bronchial/pulmonary mucosa, mucosa of oral cavity, rectal mucosa, vaginal mucosa, and the like, and nasal mucosa is most preferred.

The composition of the present invention may be formulated in a dosage form suitable for administration as a pharmaceutical preparation. It may contain an indirect dosage form such as an oral formulation for administration to the gastric and intestinal mucosa, but the composition of the present invention is preferably administered directly to the mucosa, and most preferably it takes a dosage form that can be sprayed as a mist. In this case, the composition of the present invention may be filled in a gastric or enteric capsule, for example, and the composition is exposed at the desired site of mucosa. As another dosage form, when given to the rectal mucosa, the present invention may be filled in a capsule in a unit dosage form, which is administered as a suppository. When given to the oral mucosa, nasal mucosa, or vaginal mucosa, the composition of the present invention may be filled in a spray-type container, a fixed amount of which is sprayed to the oral cavity, nose, or vagina. When given to the tracheal/bronchial/pulmonary mucosa, the present invention may be filled to an inhalation-type container, which is allowed to be inhaled into the trachea, bronchus, or lung.

EXAMPLES

The present invention will now be explained with reference to the following examples.

Fluorescein and carboxy fluorescein used in the present invention are substances generally used as a model drug of the liposoluble low molecular weight drug and of the water-soluble low molecular weight drug, respectively. As an example of the water-soluble high molecular weight drug, salmon calcitonin was used. Fluorescein was obtained from Wako Pure Chemicals, 5-carboxy fluorescein was from Molecular Probes, salmon calcitonin was from Bachem, crystalline cellulose carmellose sodium was from Aviel™ RC-591NF manufactured by Asahi Chemical Industry, Co., Ltd., Polysorbate 80 was from Wako Pure Chemicals, benzalkonium chloride was from Nakalai Tesque, glucose was from Wako Pure Chemicals, sodium chloride was from Wako Pure Chemicals, caroboxymethyl cellulose sodium was from Wako Pure Chemicals, carbazochrome was from Wako Pure Chemicals, tranexamic acid was from Wako Pure Chemicals.

Example 1

Fluorescein composition Nos. 1 to 10 for application to the mucosa comprising the components described in the following Table 1 were prepared. For each pharmaceutical preparation, osmotic pressure was measured using the Micro-Osmometer Model 3MO from Advance Instruments, Inc. The result is shown in Table 1.

One hundred μl each of the compositions 1 to 10 for application to the nasal mucosa was sprayed to the unilateral nasal cavity of rabbits (Japanese White, male, weighing 3 kg) using a commercially available suspension device. At 5, 10, 15, 30, 60, and 120 minutes after the administration, 0.5 ml of the blood was taken from the ear vein and the plasma level of fluorescein was determined by HPLC. From the time-concentration curve till 120 minutes after the spraying, $AUC_{0-120\ min}$ was determined and bioavailability (B.A.) for the intravenous injection was calculated. The mean values of three rabbits are shown in Table 1.

TABLE 1

| Composition No. | Composition | Osmotic pressure (mOsm) | B.A. (%) |
|---|---|---|---|
| 1 | Fluorescein: 0.1% w/w<br>Crystalline cellulose carmellose sodium: 1.7% w/w<br>Polysorbate 80: 0.1% w/w<br>Benzalkonium chloride: 0.03% w/w | 5 | 63 |
| 2 | Fluorescein: 0.1% w/w<br>Crystalline cellulose carmellose sodium: 1.7% w/w<br>Polysorbate 80: 0.1% w/w<br>Benzalkonium chloride: 0.03% w/w<br>Sodium chloride: 0.08% w/w | 30 | 47 |
| 3 | Fluorescein: 0.1% w/w<br>Crystalline cellulose carmellose sodium: 1.7% w/w<br>Polysorbate 80: 0.1% w/w<br>Benzalkonium chloride: 0.03% w/w<br>Sodium chloride: 0.2% w/w | 72 | 16 |
| 4 | Fluorescein: 0.1% w/w<br>Crystalline cellulose carmellose sodium: 1.7% w/w<br>Polysorbate 80: 0.1% w/w<br>Benzalkonium chloride: 0.03% w/w<br>Sodium chloride: 0.4% w/w | 128 | 13 |
| 5 | Fluorescein: 0.1% w/w<br>Crystalline cellulose carmellose sodium: 1.7% w/w<br>Polysorbate 80: 0.1% w/w<br>Benzalkonium chloride: 0.03% w/w<br>Glucose: 0.5% w/w | 30 | 29 |
| 6 | Fluorescein: 0.1% w/w<br>Crystalline cellulose carmellose sodium: 1.7% w/w<br>Polysorbate 80: 0.1% w/w<br>Benzalkonium chloride: 0.03% w/w<br>Glucose: 1.2% w/w | 72 | 10 |
| 7 | Fluorescein: 0.1% w/w<br>Crystalline cellulose carmellose sodium: 1.7% w/w<br>Polysorbate 80: 0.1% w/w<br>Benzalkonium chloride: 0.03% w/w<br>Glucose: 2.1% w/w | 128 | 9 |
| 8 | Fluorescein: 0.1% w/w<br>Crystalline cellulose carmellose sodium: 0.1% w/w<br>Polysorbate 80: 0.1% w/w<br>Benzalkonium chloride: 0.03% w/w | 0 | 22 |
| 9 | Fluorescein: 0.1% w/w<br>Crystalline cellulose carmellose sodium: 0.5% w/w<br>Polysorbate 80: 0.1% w/w<br>Benzalkonium chloride: 0.03% w/w | 0 | 37 |
| 10 | Fluorescein: 0.1% w/w<br>Crystalline cellulose carmellose sodium: 3.0% w/w<br>Polysorbate 80: 0.1% w/w<br>Benzalkonium chloride: 0.03% w/w | 7 | 53 |

Comparative Example 1

Fluorescein composition Nos. 11 to 16 for application to the mucosa comprising the components described in the following Table 2 were prepared. For each pharmaceutical preparation, osmotic pressure was measured using the Micro-Osmometer Model 3MO from Advance Instruments, Inc. The result is shown in Table 2. Bioavailability (B.A.) of the compositions 11 to 16 determined by the method described in working example 1 is also shown in Table 2.

TABLE 2

| Composition No. | Composition | Osmotic pressure (mOsm) | B.A. (%) |
|---|---|---|---|
| 11 | Fluorescein: 0.1% w/w<br>Crystalline cellulose carmellose sodium: 1.7% w/w<br>Polysorbate 80: 0.1% w/w<br>Benzalkonium chloride: 0.03% w/w<br>Sodium chloride: 0.9% w/w | 290 | 7 |
| 12 | Fluorescein: 0.1% w/w<br>Crystalline cellulose carmellose sodium: 1.7% w/w<br>Polysorbate 80: 0.1% w/w | 340 | 7 |

TABLE 2-continued

| Composition No. | Composition | Osmotic pressure (mOsm) | B.A. (%) |
|---|---|---|---|
| 13 | Benzalkonium chloride: 0.03% w/w<br>Glucose: 5% w/w<br>Fluorescein: 0.1% w/w<br>Crystalline cellulose carmellose sodium: 1.7% w/w<br>Polysorbate 80: 0.1% w/w<br>Benzalkonium chloride: 0.03% w/w<br>Glucose: 67% w/w | 4000 | 4 |
| 14 | Fluorescein: 0.1% w/w<br>Carboxy methyl cellulose sodium: 0.2% w/w<br>Polysorbate 80: 0.1% w/w<br>Benzalkonium chloride: 0.03% w/w | 5 | 7 |
| 15 | Fluorescein: 0.1% w/w<br>Carboxy methyl cellulose sodium: 0.2% w/w<br>Polysorbate 80: 0.1% w/w<br>Benzalkonium chloride: 0.03% w/w<br>Sodium chloride: 0.08% w/w | 30 | 5 |
| 16 | Fluorescein: 0.1% w/w<br>Carboxy methyl cellulose sodium: 0.2% w/w<br>Polysorbate 80: 0.1% w/w<br>Benzalkonium chloride: 0.03% w/w<br>Glucose: 0.5% w/w | 30 | 5 |

Example 2

5-Carboxy fluorescein composition Nos. 17 to 18 for application to the mucosa comprising the components described in the following Table 3 were prepared. For each pharmaceutical preparation, osmotic pressure was measured using the Micro-Osmometer Model 3MO from Advance Instruments, Inc. The result is shown in Table 3. Bioavailability (B.A.) of the compositions 17 to 18 determined by the method described in Working example 1 is also shown in Table 3.

TABLE 3

| Composition No. | Composition | Osmotic pressure (mOsm) | B.A. (%) |
|---|---|---|---|
| 17 | 5-carboxy fluorescein: 0.1% w/w<br>Crystalline cellulose carmellose sodium: 1.7% w/w<br>Polysorbate 80: 0.1% w/w<br>Benzalkonium chloride: 0.03% w/w | 6 | 52 |
| 18 | 5-carboxy fluorescein: 0.1% w/w<br>Crystalline cellulose carmellose sodium: 1.7% w/w<br>Polysorbate 80: 0.1% w/w<br>Benzalkonium chloride: 0.03% w/w<br>Glucose: 0.4% w/w | 30 | 47 |

Comparative Example 2

5-Carboxy fluorescein composition Nos. 19 to 22 for application to the mucosa comprising the components described in the following Table 4 were prepared. For each pharmaceutical preparation, osmotic pressure was measured using the Micro-Osmometer Model 3MO from Advance Instruments, Inc. The result is shown in Table 4. Bioavailability (B.A.) of the compositions 19 to 22 determined by the method described in Working example 1 is also shown in Table 4.

TABLE 4

| Composition No. | Composition | Osmotic pressure (mOsm) | B.A. (%) |
|---|---|---|---|
| 19 | 5-carboxy fluorescein: 0.1% w/w<br>Crystalline cellulose carmellose sodium: 1.7% w/w<br>Polysorbate 80: 0.1% w/w<br>Benzalkonium chloride: 0.03% w/w<br>Glucose: 5% w/w | 340 | 5 |
| 20 | 5-carboxy fluorescein: 0.1% w/w<br>Crystalline cellulose carmellose sodium: 1.7% w/w<br>Polysorbate 80: 0.1% w/w<br>Benzalkonium chloride: 0.03% w/w<br>Glucose: 67% w/w | 4000 | 3 |
| 21 | 5-carboxy fluorescein: 0.1% w/w<br>Carboxy methyl cellulose sodium: 0.2% w/w<br>Polysorbate 80: 0.1% w/w<br>Benzalkonium chloride: 0.03% w/w | 6 | 7 |
| 22 | 5-carboxy fluorescein: 0.1% w/w<br>Carboxy methyl cellulose sodium: 0.2% w/w<br>Polysorbate 80: 0.1% w/w<br>Benzalkonium chloride: 0.03% w/w<br>Glucose: 0.4% w/w | 30 | 3 |

Example 3

Salmon calcitonin composition Nos. 23 to 24 for application to the mucosa comprising the components described in the following Table 5 were prepared. For each pharmaceutical preparation, osmotic pressure was measured using the Micro-Osmometer Model 3MO from Advance Instruments, Inc. The result is shown in Table 5. Bioavailability (B.A.) of the compositions 23 to 24 determined by the method described in Working example 1 is also shown in Table 5.

TABLE 5

| Composition No. | Composition | Osmotic pressure (mOsm) | B.A. (%) |
|---|---|---|---|
| 23 | Salmon calcitonin: 0.008% w/w<br>Crystalline cellulose carmellose sodium: 1.7% w/w<br>Polysorbate 80: 0.1% w/w<br>Benzalkonium chloride: 0.03% w/w | 10 | 52 |
| 24 | Salmon calcitonin: 0.008% w/w<br>Crystalline cellulose carmellose sodium: 1.7% w/w<br>Polysorbate 80: 0.1% w/w<br>Benzalkonium chloride: 0.03% w/w<br>Glucose: 0.4% w/w | 30 | 47 |

Comparative Example 3

Salmon calcitonin composition Nos. 25 to 28 for application to the mucosa comprising the components described in the following Table 6 were prepared. For each pharmaceutical preparation, osmotic pressure was measured using the Micro-Osmometer Model 3MO from Advance Instruments, Inc. The result is shown in Table 6. Bioavailability (B.A.) of the compositions 25 to 28 determined by the method described in working example 1 is also shown in Table 6.

TABLE 6

| Composition No. | Composition | Osmotic pressure (mOsm) | B.A. (%) |
|---|---|---|---|
| 25 | Salmon calcitonin: 0.008% w/w<br>Crystalline cellulose carmellose sodium: 1.7% w/w<br>Polysorbate 80: 0.1% w/w<br>Benzalkonium chloride: 0.03% w/w<br>Glucose: 5% w/w | 340 | 3 |
| 26 | Salmon calcitonin: 0.008% w/w<br>Crystalline cellulose carmellose sodium: 1.7% w/w<br>Polysorbate 80: 0.1% w/w<br>Benzalkonium chloride: 0.03% w/w<br>Glucose: 67% w/w | 4000 | 2 |
| 27 | Salmon calcitonin: 0.008% w/w<br>Caroboxymethyl cellulose sodium: 0.2% w/w<br>Polysorbate 80: 0.1% w/w<br>Benzalkonium chloride: 0.03% w/w | 6 | 5 |
| 28 | Salmon calcitonin: 0.008% w/w<br>Caroboxymethyl cellulose sodium: 0.2% w/w<br>Polysorbate 80: 0.1% w/w<br>Benzalkonium chloride: 0.03% w/w<br>Glucose: 0.4% w/w | 30 | 5 |

When the model drug is a liposoluble low molecular weight substance, fluorescein, plasma levels of fluorescein in rabbits that were sprayed with a pharmaceutical preparation having a low osmotic pressure of 5 mOsm (Composition No. 1) to the nasal mucosa were markedly higher than those in rabbits that were sprayed with a pharmaceutical preparation having an almost isotonic osmotic pressure of 340 mOsm (Composition Nos. 11 and 12) or with a pharmaceutical preparation having a high osmotic pressure of 4000 mOsm (Composition No. 13), and, as shown in Table 1, the bioavailability is increased by 8 to 15 fold. Bioavailability decreases with increased osmotic pressure, and at 30 mOsm (Composition No. 2) it is three-fourth that of 5 mOsm (Composition No. 1) and at a higher 72 mOsm (Composition No. 3) it decreases to a great extent. Even at 128 mOsm (Composition No. 4) it exhibits a bioavailability about twice as high as that of the pharmaceutical preparation having 290 mOsm or greater (Composition Nos. 11 to 13). It has been also shown that even when isotonic at low osmotic pressure, salts such as sodium chloride (Composition Nos. 2 to 4) have higher bioavailability than water-soluble salts such as glucose (Composition Nos. 5 to 7). Furthermore, it indicates that up to about 1.5%, the higher the concentration of the water-insoluble or low water soluble substances is, the higher the bioavailability is (comparison between Composition Nos. 8 and 9 and Composition No. 1). Even for the pharmaceutical preparations having a low osmotic pressure, plasma levels were almost equal to the pharmaceutical preparations having isotonic or high osmotic pressure when they do not contain water-insoluble or low water soluble substances (Composition Nos. 14 to 16). These results indicate that the effect of osmotic pressure of the pharmaceutical preparation which is isotonic or lower on the permeability of the low water soluble substance to the blood at the mucosa is markedly exhibited only when a water-insoluble or low water soluble substance is included, and thereby the effect of the aqueous pharmaceutical composition of the present invention for application to the mucosa was demonstrated.

When the model drug is a water-soluble low molecular weight substance, 5-carboxy fluorescein, plasma levels of 5-carboxy fluorescein in rabbits that were sprayed with a pharmaceutical preparation having a low osmotic pressure of 6 mOsm (Composition No. 17) to the nasal mucosa were markedly higher than those in rabbits that were sprayed with a pharmaceutical preparation having an almost isotonic osmotic pressure of 340 mOsm (Composition Nos. 19) or with a pharmaceutical preparation having a high osmotic pressure of 4000 mOsm (Composition No. 20), and, as shown in Table 3, the bioavailability is increased by 9 to 17 fold. Furthermore, even for the pharmaceutical preparations having a low osmotic pressure, plasma levels were almost equal to the pharmaceutical preparations having isotonic or high osmotic pressure when they do not contain a water-insoluble or low water soluble substance (Composition Nos. 21 to 22).

These results indicate that the effect of osmotic pressure of the pharmaceutical preparation which is isotonic or lower on the permeability of the low water soluble substance to the blood at the mucosa is markedly exhibited only when a water-insoluble or low water soluble substance is included, and thereby the effect of the aqueous pharmaceutical composition of the present invention for application to the mucosa was demonstrated.

When the drug is a water-soluble high molecular weight salmon calcitonin, plasma levels of salmon calcitonin in rabbits that were sprayed with a pharmaceutical preparation having a low osmotic pressure of 10 mOsm (Composition No. 23) to the nasal mucosa were markedly higher than those in rabbits that were sprayed with a pharmaceutical preparation having an almost isotonic osmotic pressure of 340 mOsm (Composition Nos. 25) or with a pharmaceutical preparation having a high osmotic pressure of 4000 mOsm (Composition No. 26), and, as shown in Table 5, the bioavailability is increased by 13 to 19 fold.

Even for the pharmaceutical preparations having a low osmotic pressure, plasma levels were almost equal to the pharmaceutical preparations having isotonic or high osmotic pressure when they do not contain a water-insoluble or low water soluble substance (Composition Nos. 27 and 28).

These results indicate that the effect of osmotic pressure of the pharmaceutical preparation which is isotonic or lower on the permeability of the low water soluble substance to the blood at the mucosa is markedly exhibited only when a water-insoluble or low water soluble substance is included, and thereby the effect of the aqueous pharmaceutical composition of the present invention for application to the mucosa was demonstrated.

Figure 2:
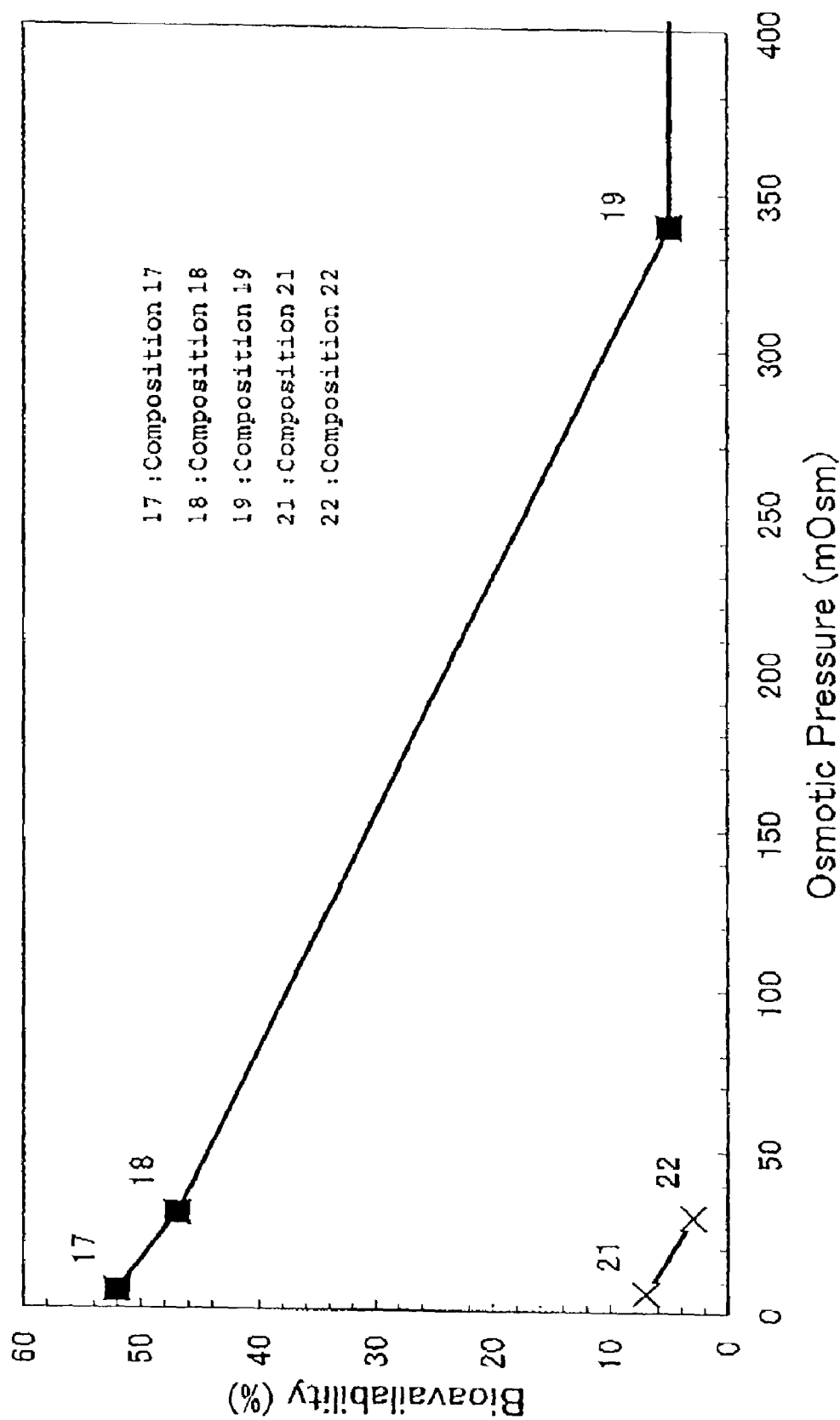
FIG. 2 is a graph showing the relationship between osmotic pressure and bioavailability in the result that compares the absorptivity of 5-carboxy fluorescein in Working example 2 and Comparative example 2.
Figure 3:
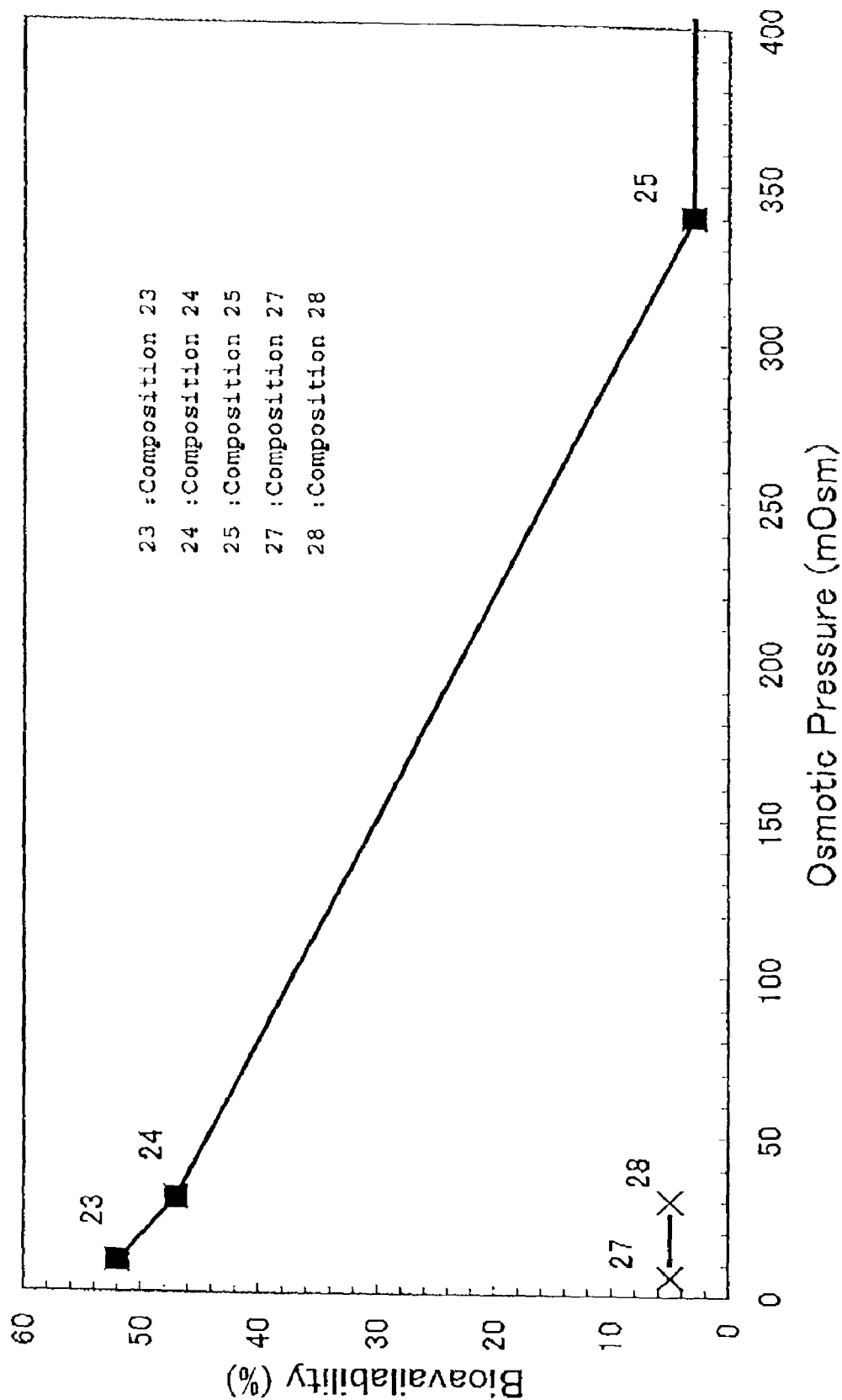
FIG. 3 is a graph showing the relationship between osmotic pressure and bioavailability in the result that compares the absorptivity of salmon calcitonin in Working example 3 and Comparative example 3.

With regard to the result that compares the absorptivity of fluorescein in Example 1 and Comparative example 1, the relationship between the osmotic pressure and bioavailability is shown in FIG. 1. Also, with regard to the result that compares the absorptivity of 5-carboxy fluorescein in Example 2 and Comparative example 2, the relationship between the osmotic pressure and bioavailability is shown in FIG. 2. Also, with regard to the result that compares the absorptivity of salmon calcitonin in Example 3 and Comparative example 3, the relationship between the osmotic pressure and bioavailability is shown in FIG. 3. It is apparent that in any of the drugs, bioavailability increases with decreased osmotic pressure and that a water-insoluble and/or low water soluble substance represented by crystalline cellulose carmellose sodium is required to obtain a high bioavailability.

FIG. 4 is a photograph that shows the expansion of the composition when the composition of the present invention having an osmotic pressure of 10 mOsm and that having an osmotic pressure of 290 mOsm (isotonic) were added to the physiological saline having the same osmotic pressure as the mucus on the mucosa (thus, simulating mucus). The figure shows that the composition of the present invention having a low osmotic pressure remain at the addition site whereas the isotonic compositions easily disperse.

Example 4

Fluorescein composition Nos. 29 to 33 for application to the mucosa comprising the components described in the following Table 7 were prepared. For each pharmaceutical preparation, osmotic pressure was measured using the Micro-Osmometer Model 3MO from Advance Instruments, Inc. The result is shown in Table 7. Bioavailability (B.A.) of the composition Nos. 29 to 33 determined by the method described in Working example 1 is also shown in Table 7. 120 minutes after this, blood was drawn from the rabbits, the nasal cavity was washed with 500 ml of 4 mM NaOH solution in water, and then the concentration of fluorescein in the wash solution was determined by HPLC. The amount of fluorescein in the wash solution relative to the amount given was calculated as a residual ratio in the nasal cavity, and the mean residual ratio in the nasal cavity for three rabbits is shown in Table 7.

TABLE 7

| Composition No. | Composition | Osmotic pressure (mOsm) | residual ratio in nasal cavity (%) | B.A. (%) |
|---|---|---|---|---|
| 29 | Fluorescein: 0.1% w/w<br>Carbazochrome: 0.1% w/w<br>Crystalline cellulose carmellose sodium: 1.7% w/w<br>Polysorbate 80: 0.1% w/w<br>Benzalkonium chloride: 0.03% w/w | 5 | 49 | 30 |
| 30 | Fluorescein: 0.1% w/w<br>Carbazochrome: 0.1% w/w<br>Crystalline cellulose carmellose sodium: 1.7% w/w<br>Polysorbate 80: 0.1% w/w<br>Benzalkonium chloride: 0.03% w/w<br>Sodium chloride: 0.08% w/w | 30 | 32 | 22 |
| 31 | Fluorescein: 0.1% w/w<br>Carbazochrome: 0.1% w/w<br>Crystalline cellulose carmellose sodium: 1.7% w/w<br>Polysorbate 80: 0.1% w/w<br>Benzalkoniuin chloride: 0.03% w/w<br>Sodium chloride: 0.2% w/w | 72 | 10 | 10 |
| 32 | Fluorescein: 0.1% w/w<br>Carbazochrome: 0.1% w/w<br>Crystalline cellulose carmellose sodium: 1.7% w/w<br>Polysorbate 80: 0.1% w/w<br>Benzalkonium chloride: 0.03% w/w<br>Sodium chloride: 0.4% w/w | 128 | 9 | 7 |
| 33 | Fluorescein: 0.1% w/w<br>Tranexamic acid: 0.1% w/w<br>Crystalline cellulose carmellose sodium: 1.7% w/w<br>Polysorbate 80: 0.1% w/w<br>Benzalkonium chloride: 0.03% w/w | 7 | 51 | 28 |

Comparative Example 4

Fluorescein composition Nos. 34 to 38 for application to the mucosa comprising the components described in the following Table 8 were prepared. For each pharmaceutical preparation, osmotic pressure was measured using the Micro-Osmometer Model 3MO from Advance Instruments, Inc. Bioavailability (B.A.) and the residual ratio in the nasal cavity of the composition Nos. 34 to 38 determined by the method described in Working example 4 are also shown in Table 8.

TABLE 8

| Composition No. | Composition | Osmotic pressure (mOsm) | residual ratio in nasal cavity (%) | B.A. (%) |
|---|---|---|---|---|
| 34 | Fluorescein: 0.1% w/w<br>Crystalline cellulose carmellose sodium: 1.7% w/w<br>Polysorbate 80: 0.1% w/w<br>Benzalkonium chloride: 0.03% w/w | 5 | 23 | 63 |
| 35 | Fluorescein: 0.1% w/w<br>Crystalline cellulose carmellose sodium: 1.7% w/w<br>Polysorbate 80: 0.1% w/w<br>Benzalkonium chloride: 0.03% w/w<br>Sodium chloride: 0.08% w/w | 30 | 15 | 47 |
| 36 | Fluorescein: 0.1% w/w<br>Crystalline cellulose carmellose sodium: 1.7% w/w<br>Polysorbate 80: 0.1% w/w<br>Benzalkonium chloride: 0.03% w/w<br>Sodium chloride: 0.2% w/w | 72 | 5 | 16 |
| 37 | Fluorescein: 0.1% w/w<br>Crystalline cellulose carmellose sodium: 1.7% w/w<br>Polysorbate 80: 0.1% w/w<br>Benzalkonium chloride: 0.03% w/w<br>Sodium chloride: 0.4% w/w | 128 | 4 | 13 |

The residual ratio in the nasal cavity and retentivity in the nasal mucosa of the model drug fluorescein are higher by 2 to 3-fold in the Examples of the present invention (composition Nos. 29 to 33) containing a hemostatic agent (carbazochrome or tranexamic acid) than the in the Comparative examples (composition Nos. 34 to 37) containing no hemostatic agent. In particular, when osmotic pressure is as low as 5 mOsm (composition No. 29) or 7 mOsm (composition No. 33), residual ratio in the nasal cavity is very high at about 50%. The result indicates that a drug, that permeates into the blood after a single administration of the drug, stays at the mucosa without permeating into the blood when coadministered with a hemostatic agent, and thereby the usefulness of the present invention has been shown for the drugs of which efficacy depends on the amount of the drug and on the time of retention at the local mucosa which may lead to side effects. Furthermore, it has been shown that the amount remaining in the mucosa is greater for the pharmaceutical preparations having low osmotic pressure for which the amount permeated to the blood is greater, and therefore the usefulness of the present invention becomes even greater when the pharmaceutical preparation has a low osmotic pressure.

INDUSTRIAL APPLICABILITY

Thus, the first aspect of the present invention provides a composition for application to the mucosa which has efficient and high permeability of the drug through the mucosa to the blood. By using such a composition of the present invention for application to the mucosa, effects equal to or greater than those obtained with the conventional compositions can be obtained even at smaller doses or smaller administration frequencies than the conventional methods. This can lead to reduction in side effects.

The second aspect of the present invention provides a composition for application to the mucosa which has efficient and/high permeability to the blood and retentivity at the mucosa. By using such a composition of the present invention for application to the mucosa, effects equal to or greater than those obtained with the conventional compositions can be obtained even at smaller doses or lower administration frequencies than the conventional methods. This can lead to reduction in side effects.

Thus, the present invention extremely useful in terms of therapeutic and economic effects for drug therapies that employ application to the mucosa.

The invention claimed is:

1. An aqueous pharmaceutical composition for application to the mucosa, comprising one or more water-insoluble and/or low water soluble substance, and one or more medicament, and having an osmotic pressure of 150 mOsm or less.

2. An aqueous pharmaceutical composition for application to the mucosa comprising one or more hemostatic agent, one or more water-insoluble and/or low water soluble substance, and one or more medicament, and having an osmotic pressure of 150 mOsm or less, wherein said hemostatic agent is one or more selected from the group consisting of tranexamic acid, epsilon aminocaproic acid, carbazochrome, carbazochrome sulfonate, carbazochrome sodium sulfonate, phytonadione, etamsylate, monoethanol amine oleate, thrombin, hemocoaglase, and adrenochrome monoaminoguanidine mesilate.

3. The pharmaceutical composition for application to the mucosa according to claim 1 or 2, wherein said osmotic pressure is 90 mOsm or less.

4. The pharmaceutical composition for application to the mucosa according to claim 1, further comprising an osmotic pressure-controlling agent.

5. The pharmaceutical composition for application to the mucosa according to claim 4, wherein said osmotic pressure-controlling agent is a salt.

6. The pharmaceutical composition for application to the mucosa according to claim 4, wherein said osmotic pressure-controlling agent is sodium chloride.

7. The pharmaceutical composition for application to the mucosa according to claim 4, wherein said osmotic pressure-controlling agent is a water-soluble sugar.

8. The pharmaceutical composition for application to the mucosa according to claim 4, wherein said osmotic pressure-controlling agent is glucose.

9. The pharmaceutical composition for application to the mucosa according to claim 1, wherein said water-insoluble and/or low water soluble substance is a cellulose.

10. The pharmaceutical composition for application to the mucosa according to claim 9, wherein said cellulose is crystalline cellulose.

11. The pharmaceutical composition for application to the mucosa according to claim 1 or 2, wherein said one or more water-insoluble and/or low water soluble substance is present as solid particles in an aqueous medium.

12. The pharmaceutical composition for application to the mucosa according to claim 1 or 2 wherein said one or more water-insoluble and/or low water soluble substance is homogeneously dispersed as solid particles in an aqueous medium.

13. The pharmaceutical composition for application to the mucosa according to claim 1 or 2, further comprising a water-soluble polymer substance.

14. The pharmaceutical composition for application to the mucosa according to claim 13, wherein said water-soluble polymer is one or more selected from the group consisting of alginic acid, polyethylene glycol, glycerin, polyoxyethylene polyoxypropylene glycol, propylene glycol, pectin, low methoxyl pectin, guar gum, gum arabic, carrageenan, methyl cellulose, carboxymethyl cellulose sodium, xanthan gum, hydroxypropyl cellulose, and hydroxypropyl methyl cellulose.

15. The pharmaceutical composition for application to the mucosa according to claim 13, wherein said water-soluble polymer is carboxymethyl cellulose sodium.

16. The pharmaceutical composition for application to the mucosa according to claim 13, wherein said water-soluble polymer is xanthan gum.

17. The pharmaceutical composition for application to the mucosa according to claim 13, wherein said water-soluble polymer is hydroxypropyl methyl cellulose.

18. The pharmaceutical composition for application to the mucosa according to claim 13, wherein the combination of said water-insoluble substance and water-soluble polymer is crystalline cellulose carmellose sodium.

19. The pharmaceutical composition for application to the mucosa according to claim 1 or 2, further comprising a surfactant.

20. The pharmaceutical composition for application to the mucosa according to claim 19, wherein said surfactant is polyoxyethylene (20) sorbitan monooleate.

21. The pharmaceutical composition for application to the mucosa according to claim 1 or 2, wherein said medicament is a water-soluble medicament.

22. The pharmaceutical composition for application to the mucosa according to claim 1 or 2, wherein said medicament is a liposoluble medicament.

23. The pharmaceutical composition for application to the mucosa according to claim 1 or 2, wherein said mucosa is nasal mucosa.

24. The pharmaceutical composition for application to the mucosa according to claim 2, wherein the medicament is one or more selected from the group consisting of an antiallergic agent, an antihistamic agent, an anticholinergic agent, a steroid, a vaccine, and a substance for gene therapy, and the mucosa is nasal mucosa.

25. The pharmaceutical composition for application to nasal mucosa according to claim 24, wherein the medicament is a steroid.

26. An aqueous pharmaceutical nasal composition for application to the mucosa, comprising one or more hemostatic agent, one or more water-insoluble and/or low water soluble substance, and one or more medicament, and having an osmotic pressure of 150 mOsm or less.

27. The pharmaceutical composition according to claim 1, wherein the concentration of water-insoluble and/or low water soluble substance is 1% w/w to 10% w/w relative to the total amount of the pharmaceutical composition and the concentration of the medicament is 0.01% w/w to 1% w/w relative to the total amount of the pharmaceutical composition.

28. The composition according to claim 3, wherein the concentration of water-insoluble and/or low water soluble substance is 1% w/w to 10% w/w relative to the total amount of the pharmaceutical composition and the concentration of the medicament is 0.01% w/w to 1% w/w relative to the total amount of the pharmaceutical composition.

29. The pharmaceutical composition according to claim 2, wherein the concentration of water-insoluble and/or low water soluble substance is 1% w/w to 10% w/w relative to the total amount of the pharmaceutical composition and the concentration of the medicament is 0.01% w/w to 1% w/w relative to the total amount of the pharmaceutical composition.

* * * * *